(12) United States Patent
Specht et al.

(10) Patent No.: US 10,092,766 B2
(45) Date of Patent: Oct. 9, 2018

(54) CAPACITOR AND METHOD TO MANUFACTURE THE CAPACITOR

(71) Applicant: Heraeus Precious Metals GmbH & Co. KG, Hanau (DE)

(72) Inventors: Heiko Specht, Hanau (DE); Jacob Markham, Vadnais Heights, MN (US); Goran Pavlovic, Schaafheim (DE); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 468 days.

(21) Appl. No.: 14/359,813

(22) PCT Filed: Nov. 13, 2012

(86) PCT No.: PCT/EP2012/004703
§ 371 (c)(1),
(2) Date: May 21, 2014

(87) PCT Pub. No.: WO2013/075798
PCT Pub. Date: May 30, 2013

(65) Prior Publication Data
US 2014/0328004 A1   Nov. 6, 2014

(30) Foreign Application Priority Data
Nov. 23, 2011  (DE) .................. 10 2011 119 125

(51) Int. Cl.
*H01G 4/35* (2006.01)
*A61N 1/375* (2006.01)
(Continued)

(52) U.S. Cl.
CPC ............ *A61N 1/3754* (2013.01); *A61N 1/362* (2013.01); *B29C 65/48* (2013.01); *H01G 2/02* (2013.01);
(Continued)

(58) Field of Classification Search
CPC ............ H01G 4/30; H01G 4/228; H01G 4/12; H01G 4/008; H01G 4/35; H01G 4/0085; H01G 4/005; H01G 4/012
(Continued)

(56) References Cited

U.S. PATENT DOCUMENTS

| 3,025,441 A | 3/1962 | West |
| 3,063,144 A | 11/1962 | Palmour, III |

(Continued)

FOREIGN PATENT DOCUMENTS

| DE | 69729719 | 7/2005 |
| DE | 102006054249 | 5/2008 |

(Continued)

OTHER PUBLICATIONS

The International Search Report and the Written Opinion for International Application No. PCT/EP2012/004703 mailed Mar. 28, 2013 (13 pages).

(Continued)

*Primary Examiner* — Nguyen Ha
(74) *Attorney, Agent, or Firm* — Dicke, Billig & Czaja, PLLC (57) ABSTRACT

One aspect is a capacitor, having a multitude of parallel insulator layers in one stack direction, made of an electrically non-conducting material, a multitude of conductor layers alternatingly stacked with the insulator layers in the direction of the stack made from a conductive material and at least one contact body. At least some of the conductor layers are connected to one another in a conductive manner via the contact body. The contact body extends through breaks form several insulator layers, where at least the insulator layers are made of a sintered material;

(Continued)

the contact body is manufactured at least partially from a sintered material, which is introduced into the breaks in the insulator layers in an unsintered, malleable state.

17 Claims, 2 Drawing Sheets

(51) Int. Cl.
*H01G 4/30* (2006.01)
*H01G 4/008* (2006.01)
*A61N 1/362* (2006.01)
*B29C 65/48* (2006.01)
*H01G 2/02* (2006.01)
*B29L 31/34* (2006.01)

(52) U.S. Cl.
CPC ............ *H01G 4/0085* (2013.01); *H01G 4/30* (2013.01); *H01G 4/35* (2013.01); *B29L 2031/34* (2013.01)

(58) Field of Classification Search
USPC ... 361/301.4, 301, 2, 303–305, 306.1, 306.3
See application file for complete search history.

(56) References Cited

U.S. PATENT DOCUMENTS

| | | |
|---|---|---|
| 3,646,405 A | 2/1972 | Wallis et al. |
| 3,979,187 A | 9/1976 | Scherer |
| 4,152,540 A | 5/1979 | Duncan et al. |
| 4,159,075 A | 6/1979 | Ljung et al. |
| 4,217,137 A | 8/1980 | Kraska et al. |
| 4,225,262 A | 9/1980 | Koop et al. |
| 4,315,054 A | 2/1982 | Sack et al. |
| 4,354,964 A | 10/1982 | Hing et al. |
| 4,488,673 A | 12/1984 | Hopper, Jr. |
| 4,602,956 A | 7/1986 | Partlow et al. |
| 4,678,868 A | 7/1987 | Kraska et al. |
| 4,991,582 A | 2/1991 | Byers et al. |
| 5,043,535 A | 8/1991 | Lin |
| 5,515,604 A | 5/1996 | Horine et al. |
| 5,735,884 A | 4/1998 | Thompson et al. |
| 5,738,270 A | 4/1998 | Malmgren |
| 5,769,874 A | 6/1998 | Dahlberg |
| 5,796,019 A | 8/1998 | Lupton et al. |
| 5,861,714 A | 1/1999 | Wei et al. |
| 5,870,272 A | 2/1999 | Seifried et al. |
| 6,093,476 A | 7/2000 | Horiuchi et al. |
| 6,414,835 B1 | 7/2002 | Wolf et al. |
| 6,490,148 B1* | 12/2002 | Allen .................. A61N 1/3754 361/302 |
| 6,643,903 B2 | 11/2003 | Stevenson et al. |
| 6,660,116 B2 | 12/2003 | Wolf et al. |
| 6,841,731 B1 | 1/2005 | Zanello |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,260,434 B1 | 8/2007 | Lim et al. |
| 7,274,963 B2 | 9/2007 | Spadgenske |
| 7,341,802 B1 | 3/2008 | Ota et al. |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,630,768 B1 | 12/2009 | Coffed et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,143,697 B2* | 3/2012 | Seh .................. H05K 1/162 257/532 |
| 8,163,397 B2 | 4/2012 | Ok et al. |
| 8,179,658 B2 | 5/2012 | Brendel et al. |
| 8,288,654 B2 | 10/2012 | Taylor et al. |
| 8,326,425 B2 | 12/2012 | Sprain et al. |
| 8,346,362 B2 | 1/2013 | Kinney et al. |
| 8,355,785 B1 | 1/2013 | Hammond et al. |
| 8,378,239 B2 | 2/2013 | Lakner et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,538,530 B1 | 9/2013 | Orinski |
| 8,552,311 B2 | 10/2013 | Koester et al. |
| 8,626,310 B2 | 1/2014 | Barror et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,825,162 B2 | 9/2014 | Reisinger |
| 8,894,914 B2 | 11/2014 | Pavlovic |
| 9,032,614 B2 | 5/2015 | Specht |
| 9,040,819 B2 | 5/2015 | Kempf et al. |
| 9,048,608 B2 | 6/2015 | Pavlovic |
| 9,088,093 B2 | 7/2015 | Reisinger et al. |
| 9,306,318 B2 | 4/2016 | Reisinger |
| 2001/0013756 A1 | 8/2001 | Mori et al. |
| 2002/0166618 A1 | 11/2002 | Wolf et al. |
| 2003/0053284 A1* | 3/2003 | Stevenson ............. H01G 4/35 361/302 |
| 2003/0178726 A1* | 9/2003 | Ogawa ............. H01L 21/4857 257/758 |
| 2004/0066603 A1* | 4/2004 | Saito .................. H01G 4/30 361/302 |
| 2004/0116976 A1 | 6/2004 | Spadgenske |
| 2004/0128016 A1 | 7/2004 | Stewart |
| 2004/0257749 A1* | 12/2004 | Otsuka .................. H01G 2/065 361/306.3 |
| 2005/0132548 A1* | 6/2005 | Choo .................. H01G 4/005 29/25.03 |
| 2006/0247714 A1 | 11/2006 | Taylor et al. |
| 2006/0259093 A1 | 11/2006 | Stevenson et al. |
| 2007/0183118 A1 | 8/2007 | Fu et al. |
| 2007/0217121 A1 | 9/2007 | Fu |
| 2008/0060834 A1 | 3/2008 | Eck et al. |
| 2008/0060844 A1 | 3/2008 | Teske et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0247117 A1 | 10/2008 | Elam et al. |
| 2008/0269831 A1 | 10/2008 | Erickson |
| 2009/0192578 A1 | 7/2009 | Biggs |
| 2009/0207550 A1 | 8/2009 | Feichtinger et al. |
| 2009/0281586 A1 | 11/2009 | Lim |
| 2010/0023086 A1 | 1/2010 | Lim |
| 2010/0109966 A1 | 5/2010 | Mateychuk et al. |
| 2010/0258342 A1 | 10/2010 | Parker |
| 2011/0000699 A1 | 1/2011 | Bealka et al. |
| 2011/0029036 A1 | 2/2011 | Yamamoto et al. |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0106205 A1* | 5/2011 | Reiterer ............. A61N 1/3754 607/37 |
| 2011/0186349 A1 | 8/2011 | Troetzschel et al. |
| 2012/0127627 A1 | 5/2012 | Brendel et al. |
| 2012/0193117 A1 | 8/2012 | Specht et al. |

(56) References Cited

U.S. PATENT DOCUMENTS

| | | | |
|---|---|---|---|
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2013/0289681 A1* | 10/2013 | Iyer .................. A61N 1/3754 607/115 |
| 2014/0262494 A1 | 9/2014 | Reisinger et al. |
| 2014/0343648 A1 | 11/2014 | Specht et al. |
| 2014/0368298 A1 | 12/2014 | Reisinger |
| 2015/0122875 A1 | 5/2015 | Pavlovic et al. |

FOREIGN PATENT DOCUMENTS

| | | |
|---|---|---|
| DE | 102008021064 | 10/2009 |
| DE | 102011009859 | 1/2011 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102005022142 | 12/2011 |
| EP | 0877400 | 11/1998 |
| EP | 1509931 | 3/2006 |
| EP | 1685874 | 8/2006 |
| EP | 1754511 | 2/2007 |
| WO | 03073450 | 9/2003 |
| WO | 03100793 | 12/2003 |
| WO | 2004110555 | 12/2004 |
| WO | 2008103166 | 8/2008 |
| WO | 2010091435 | 8/2010 |

OTHER PUBLICATIONS

The International Search Report and the Written Opinion for International Application No. PCT/EP2012/004702 mailed Mar. 28, 2013 (11 pages).

The Restriction Requirement for the U.S. Appl. No. 14/359,732 mailed Jul. 8, 2015 (8 pages).

The Office Action for the U.S. Appl. No. 14/359,732 dated Sep. 30, 2015 (11 pages).

The Final Office Action for the U.S. Appl. No. 14/359,732 dated Mar. 17, 2016 (6 pages).

The Advisory Action for the U.S. Appl. No. 14/359,732 dated May 25, 2016 (3 pages).

\* cited by examiner

CAPACITOR AND METHOD TO MANUFACTURE THE CAPACITOR

CROSS REFERENCE TO RELATED APPLICATION

This Utility Patent Application claims the benefit of the filing date of German Application No. DE 10 2011 119 125.2, filed Nov. 23, 2011, and International Application No. PCT/E2012/004703, filed Nov. 13, 2012, both of which are herein incorporated by reference.

BACKGROUND

One aspect refers to a capacitor, a procedure to manufacture this capacitor as well as a contact array with a capacitor, according to one embodiment to be used in the housing of a medically implantable device.

U.S. Pat. No. 7,564,674 2 describes a contact array with a feedthrough that is suitable for the implantation of a medical device which is connected to a capacitor to filter electrical signals. Here, solid metal contact pins run through the feedthrough as well as conductively contacted hollow channels in the filter capacitor adjacent to the feedthrough. The contact pins are connected to the hollow channels in the filter capacitor by soldering.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further features and of the can be derived from the following execution example as well as from the attached claims.

DETAILED DESCRIPTION OF THE DRAWINGS

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment is intended to produce a capacitor that can be manufactured in a simple and cost-effective manner.

Another purpose of one embodiment is to produce a capacitor that can very easily be connected electrically and mechanically to an electrical feedthrough by means of a flip chip technology.

Another purpose of one embodiment is intended to produce a capacitor that is mechanically durable and features a long product life.

Another purpose of one embodiment at hand is intended to produce a capacitor, according to the embodiment, that can be manufactured with a process safe and cost-effective procedure.

Another purpose of one embodiment at hand is to produce a contact array to be used in the housing of a medically implantable device, which is capable of cost-effectively and reliably conducting and filtering an electrical signal.

This purpose as well as other purposes is solved by various embodiment.

A capacitor according to one embodiment includes a multitude of insulator layers that are parallel in one stacking direction, consisting of an electrically non-conducting material, a multitude of alternatively layered insulators in the direction of the stack and conductor layers made of a conductive material, and at least one conductive contact body, where at least some of the conductor layers are connected to each other via the contact body, and where the contact body extends through breaks of several insulator layers, where at least the insulator layers are manufactured from a sintered material, and where the contact body is manufactured at least partially from a sintered material, which is introduced into the breaks in the insulator layers in an unsintered, malleable state.

Based on the layout of the contact body, which is made of sintered material, it is generally possible to manufacture the entire capacitor including the contact body, in one sintering process. One single sintering process is especially preferable in one embodiment.

Especially, with a capacitor according to one embodiment, you do not need to guide every metallic contact pin through a hollow space in the capacitor following the sintering of the capacitor.

A capacitor according to one embodiment is every electrical component that includes at least one electrical capacity. Therefore, it is possible according to one embodiment, that the capacitor includes an integrated inductivity and/or an Ohm resistor and/or an active electrical element in addition to the capacity.

Insulator layers and conductor layers, according to one embodiment, are surface routed layers of especially constant thickness that possess a defined exterior outline. In the normal case, the layers cover one level only. For certain variations of embodiments, the layers can also feature a defined curvature.

Depending on the execution of the embodiment, one or more contact bodies may be present in the stack of layers.

The contact bodies can be electrically connected to different groups of conductor layers, respectively. At least one contact body will extend to an exterior room, so that a line of the capacitor can be connected to the contact body.

The electrically non-conductive material of the insulator layers is in one embodiment a material made of a defined, especially high dielectricity constant. A functionally effective addition to the material could be barium titanate. For example, the EP 1 509 931 B1 describes a dielectric assembly on the basis of barium titanate, by means of which layered components can be unbreakably sintered with electrodes made of silver.

For one type of array of one embodiment, the entire contact body is positioned perpendicular to the insulator layers in a long shape. This allows a simple geometric setup of the stack made of layers. The long body can be a solid, for example, a cylindrical full body. As an alternative, or as a supplement, it could also be fashioned as a hollow body, such as a hollow cylinder.

Basically it is possible according to one embodiment, to form the contact body in its own process step into a hollow space permeated by breaks and/or other structures by introducing unsintered, malleable material and subsequently sintering it into a solid body. With an array like that, the space inside the contact body could be filled in, for example, by introducing the malleable, unsintered material by means of injectors into a hollow space into the previously built stack of layers. With a setup like this one, the contact body represents a non-structured body in the direction of the stack—prior to as well as after sintering the contact body material.

However, with one type of array according to one embodiment, the contact body is intended to be made up—at least partially—as a stack of sintered segments, where at least some of these segments are to be fashioned as a filler for one of the breaks of the insulator layers. A setup such as this one for the contact body allows a simultaneous creation of a stack made up of layers with the contact body, where a part of the contact body is intended to be inside one of those respective layers. A contact body set up in this manner can be especially beneficial to the manufacturing of a capacitor according to one embodiment. With a setup of the capacitor such as this one, the contact body is segmented in the direction of the stack—at least in an unsintered condition—thus, as a green body. This segmentation is not to be interpreted as a spatial separation in the sense at hand, but rather as any detectable or verifiable structuring. Normally, the segments of the contact body are stacked on top of each other—even in an unsintered state—and feature an electrically conductive contact.

It needs to be understood that the individual segments of the contact body, which correlate to the stacked layers inside the stack, can consist of the same or several different materials. At least in the latter case, a segmentation of the contact body will be present—even after the sintering process. However, it is important in the sense of one setup example of one embodiment that the contact body is segmented in the direction of the stack prior to the sintering process.

With one execution form of one embodiment, the conductor layers are made of a sintered material. In one embodiment, but not essential continuation of this, the insulator layers, the conductor layers and the contact body are all sintered in the course of a co-sintering process. This allows the optimization as well as the minimizing of the process steps required to manufacture the capacitor, where the common sintering of the different components creates an especially homogenous, compact electrical component with a long product life.

In the interest of a process safe optimization of the manufacturing of a capacitor according to one embodiment, it is intended for the ratio between a thickness between the insulator layers and a median diameter of the break in the insulator layer to be between 0.1 and 2. In a further embodiment, the ratio would be between 0.3 and 1.5, and in another a ratio between 0.75 and 1.25. The closer this ratio of median diameter and thickness of the break is to 1, the easier and more process safe a break can be filled with the material of the contact body. The median diameter of the break is the arithmetic median of all diameters of the break, if a cross section form of the break deviates from a circular shape. With one detail setup, the break is circular, so that the median diameter is the same as the circle diameter.

A process according to one embodiment manufactures a capacitor and includes the following steps:

a. Providing an insulator layer as a plate-shaped green body;
b. Forming the breaks inside the insulator layer;
c. Filling in the breaks with a conductive paste;
d. Placing a conductor layer on top of the insulator layer;
e. Forming a stack from a multitude of insulator layers and conductor layers on top of one another;
f. Sintering the stack.

By filling in the breaks in the insulator layers with the conductive paste, the contact body of the capacitor can be set up with different segments on top of one another, step by step, where the setup of these segments goes hand in hand with the setup of the remaining capacitor form the individual insulating and conductive layers.

Depending on the executed form, step e. describing the creation of a stack from a multitude of insulator layers and conductor layers can be executed in many different ways. Basically, it is possible to place repeated sequences of insulator layers and conductor layers on top of one another by applying insulating pastes and conductive pastes.

It is especially advantageous and effective in one embodiment to only place one conductor layer on top of an insulating layer and then to place several of these composites consisting of two layers each on top of one another to create the stack.

Basically, the individual layers of the stack can feature two or more different shapes or forms for forming the conductor layers, which are placed on top of one another in a sensible order. Thus, there can be a first form of conductor layers and a second form of conductor layers, which feature different electrical contacts; so that the conductor layers of the first form are connected to one another and the conductor layers of the second layer are connected to one another as well.

Each one of the conductor layers of the first form, for example, can be connected to the contact body and connected to an external electrical signal. The second conductor located between the respective conductor layers of the first form can all be connected to a ground line, for example. This represents the common setup of a multiple plate capacitor.

A detail setup of the process according to one embodiment includes the step of isolating a multitude of capacitors from the stack. This can take place, for example, by sawing or cutting elements out of the stack in a direction that is perpendicular to the layers, along predefined separation lines. This way, a large number of capacitors can be sintered into a single stack of layers and then be isolated afterwards.

In one detail layout, the process could feature the following step: Applying a conductive layer to a side wall of the stack, where a multitude of conductor layers is electrically connected to the conductive layer. For example, this could be conductor layers intended to be connected to a ground potential. These conductor layers, according to their shape, can overlap the separating lines when isolating the capacitors from the stack, so that the conductor layers will extend directly into the side wall of the separated capacitor after the capacitors have been separated. By applying a conductive layer, the conductive layers extending into the side wall are conductively connected to each other. An alternative execution of this process has the conductor layers that are supposed to be connected with a ground potential also connected or rather contacted by means of a contact body according to one embodiment.

One form of execution, step c. of the procedure includes the following steps:

c1. Applying a template to the insulator layer, where the template has openings covering the breaks;

c2. Applying conductive paste to the template as is done in screen printing procedures.

This allows a simple and effective filling in of the breaks with conductive material for the subsequent creation of the contact body from the different layers. The template in reference to a screen printing procedure according to one embodiment is to be understood as every structure, through which a malleable mass applied via screen printing can be spatially structured. Among other things, this could be cover plates with simple, open breaks. Especially the following known forms are also screens, where such breaks are covered with net-like structures to improve the screen printing effect, and are to be considered templates according to one embodiment.

With a simple detail layout of such a screen printing procedure, the conductive paste is evenly applied the template in a predefined thickness, where at least the surface area of the breaks is covered by the paste. Subsequently, a squeegee or another tool suitable for screen printing procedures is used to spread the material to create an even and defined spread of the applied paste through the template onto the sub layer of substrate below. Depending on the details of the layout, you can achieve that the breaks of the insulator layers are filled with the conductive paste until this paste ends flush at their surfaces, or that the paste protrudes beyond the filling of the breaks and forms a defined protrusion beyond the surface of the insulator layers.

To improve the application of the conductive paste, it is generally advantageous to support step c by creating a vacuum below the insulator layer. For this, for example, a vacuum plate might be placed underneath the insulator layer. Vacuum plates are known for their use in screen printing procedures to halter a substrate evenly and with accurate positioning. In the present case, the vacuum plate could be especially supportive to achieve a complete filling in of the breaks of this insulator layers with the conductive paste.

For a further advantageous detail layout in one embodiment, it is intended that there will be a drying process of the conductive paste between steps c2 and d. Depending on the requirements and paste systems used, this can facilitate the subsequent application of a conductive layer in step d. As an alternative, it can also be the intention that the conductor layer in step d. is applied prior to the drying of the conductive paste in the break.

In a general manner, step d of the procedure includes the following steps:

d1. Applying a template to the insulator layer, where the template has openings covering a form of the conductor layer;

d2. Applying conductive paste to the template and creating the conductor layer as is done in screen printing procedures.

This way, the conductor layer can be applied to the insulator layer in a predefined thickness and nearly any form. There is no need to mention that the application of the conductor layer can take place in one or several steps. Basically, it is also possible to apply further electrically relevant structures by means of screen printing in addition to the conductor layer to manufacture plates of the capacitor. For example, this could be an Ohm resistor, which is applied to an insulator layer by means of a paste of a defined conductivity by means of a screen printing procedure.

To improve the result of the sintering of the stack, it is intended to press the stack following step e. The pressing generally takes place after drying all layers, so that a defined compacting is achieved prior to placing the stack into a sintering oven. There is no need to mention that stacks placed on top of one another are aligned horizontally by means of controlling structures using a known procedure.

The task of one embodiment is also solved by a contact array to be used in a housing of a medically implantable device, comprising an electrical feedthrough with at least one electrically insulating feedthrough basic body and at least one electrical line element, where the line element is intended to create at least one electrically conductive connection between the interior of the housing and an exterior space through the feedthrough basic body, as well as an electrical capacitor according to one embodiment, where the line element of the feedthrough is electrically connected to the capacitor.

In one continued further formation of a contact array according to one embodiment, the line element of the feedthrough and the contact body of the capacitor are connected to one another conductively via at least one contact stud, where the contact stud consists of a soldered connection. A connection of this type allows a direct placement of the capacitor onto the feedthrough, where the contact stud represents a mechanical and electrical connection between the two structures. This way, the installation can take place analog to a flip chip technology. The contact stud is especially preferred in one embodiment as a soft solder connection with a relatively low melting point far below a sintering temperature of the capacitor. The shape of the contact stud varies depending on the requirements, for example, pillow-shaped, pillar-shaped or something of the sort.

Figure 1:
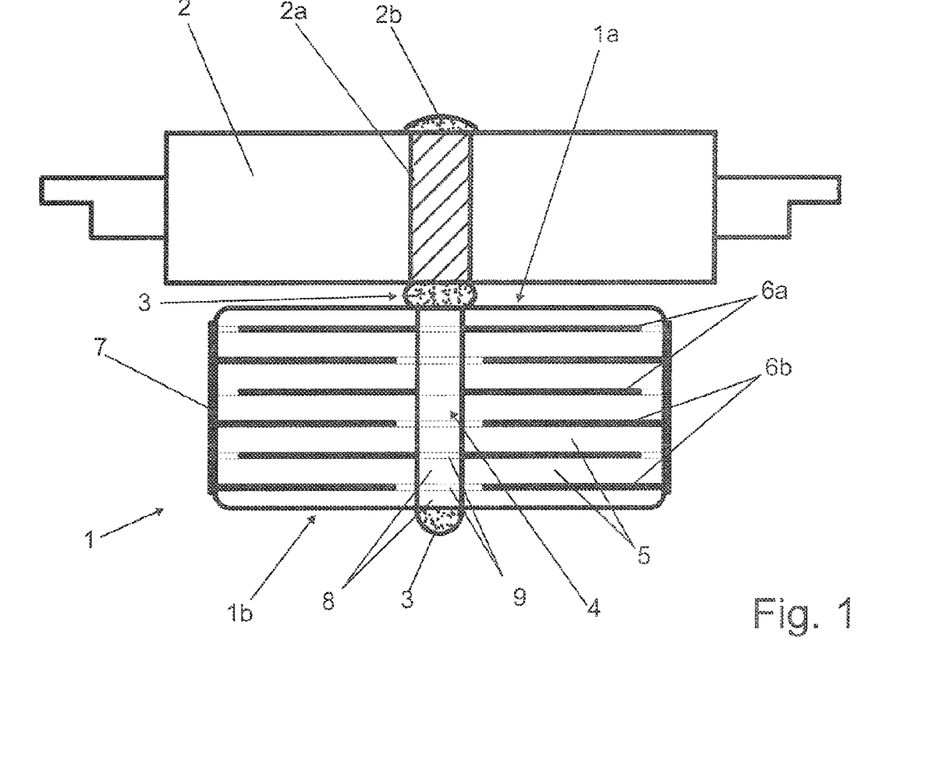
FIG. 1 illustrates a schematic cross section of a contact array according to one embodiment with a capacitor.

The contact array illustrated in FIG. 1 includes a capacitor 1 according to one embodiment as well as a feedthrough 2, where the feedthrough 2 can be installed in the housing (not illustrated) of a medically implantable device. This implantable device is in one embodiment a heart pacemaker. The feedthrough 2 features characteristics that make it suitable for implantation into a human body, such as biocompatibility, hermetic tightness and similar features. The capacitor 1 is located on the inside of the housing and does not directly contact organic tissue.

The feedthrough 2 is supposed to include a line element 2a, which leads from one exterior side of the feedthrough, starting at contact pin 2b to an interior side of the feedthrough 2. On the inside of the feedthrough, the line element 2a is connected to the contact body 4 of capacitor 1, which is continued in a straight forward direction, via a contact stud 3 consisting of a soft solderable material.

The contact body 4 is flush with a surface 1a of the capacitor 1, which faces the feedthrough 2. The contact stud 3 is placed on top of the contact body 4 or on the surface 1a of the capacitor 1.

The contact 4 completely permeates the capacitor 1 and ends flush with an opposite surface 1b, which runs parallel to the first surface 1a and faces away from the feedthrough 2. Also on this side, a contact stud 3 is placed on top of the contact body 4, which can be connected to a furthering structure such as a line wire on the inside of the housing. The capacitor 1 is formed with the contact body 4 as a whole as a layered construction, a solid body made of sinterable material.

Within the capacitor 1, the insulator layers 5 consisting of electrically non-conducting materials alternate with conductor layers 6a, 6b consisting of electrically conducting material.

In the example at hand, there are two different formations 6a, 6b of conductor layers. The first formation of conductor layers 6a is connected to the contact body 4 in the electrically conducting connection. The second formation of conductor layers 6b is not connected to the contact body via an electrically conducting connection and alternates respectively with a conductor layer of the first formation 6a ab.

The conductor layers of the second formation 6b are electrically connected to one another, in the formation present, via a conductive layer 7, which is attached to a sidewall of the capacitor 1. Here, the conductor layers of the second formation 6b extend to the edge, or rather the sidewall of the stack from layers, so that a conductor layer 7 that is placed after stacking the layers can connect all of the conductor layers 6b to one another. The conductor layer 7 can be placed before or after sintering the stack of layers of capacitor 1, depending on the requirements. In the first case, this will be in one embodiment another sinterable material, which could be, for example, made of the same material as one of the conductor layers of the second formation 6b (sinterable conductive paste).

The conductive layer 7, together with the conductor layers 6b, forms a first electrode of the capacitor, and the conductor layers 6a, together with the contact body 4, form a second electrode of the capacitor. According to the layout of the alternating parallel overlapping conductor layers 6a, 6b, there is a capacity present between the electrodes.

In general, the capacitor 1 is used to filter an electrical signal, which is conducted to the feedthrough 2 via the line element 2a. This can be an input or an output signal for example for a heart pacemaker or another implantable medical device. Further electrical elements such as Ohm resistors or inductivities or even electrically active components can be connected to the capacitor 1 or be integrated into it.

FIG. 1 illustrates the limits of the different layers, which are used to stack the capacitor 1. These are represented by dotted lines. These lines also run through the contact body 4 to clarify that the contact body 4 is made up as a stack consisting of segments 8, 9, from the insulator layers 5 and the conductor layers 6a, 6b. In the case of the insulator layers 5, a respective segment 8 of the contact body 4 is formed as a break 5a of the insulator layer 5, filled with a conductive material.

There is no need to mention that the contact body 4 can be present in its sintered state as a homogenous, non-structured body, depending on the materials used and depending on the sintering procedure. At the same time, the contact body 4 of the execution example at hand, at least prior to a completing sintering process, is presented as a stacked structure consisting of segments 5a, 6c.

Figure 2:
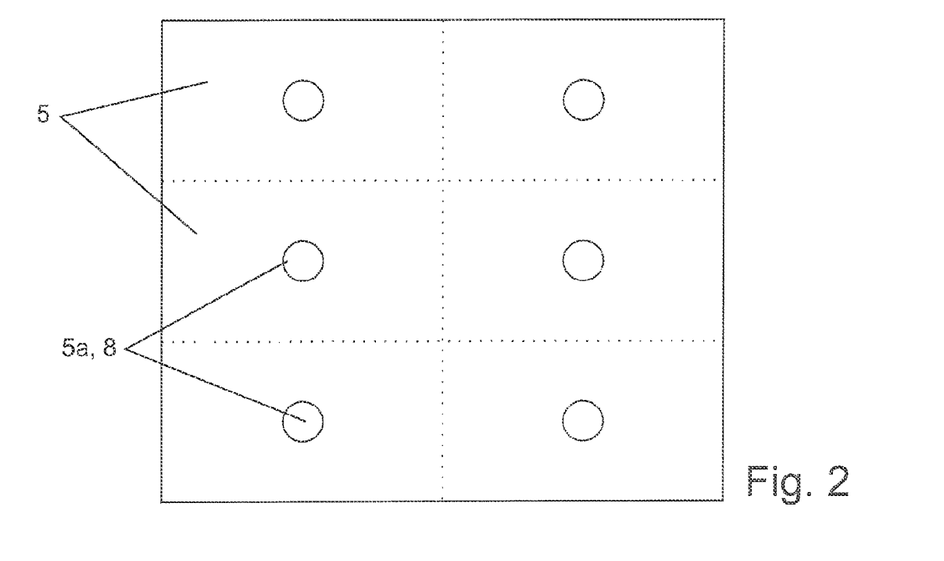
FIG. 2 illustrates a bird's eye view of an insulator layer for stack of layers that includes several capacitors.
Figure 3:
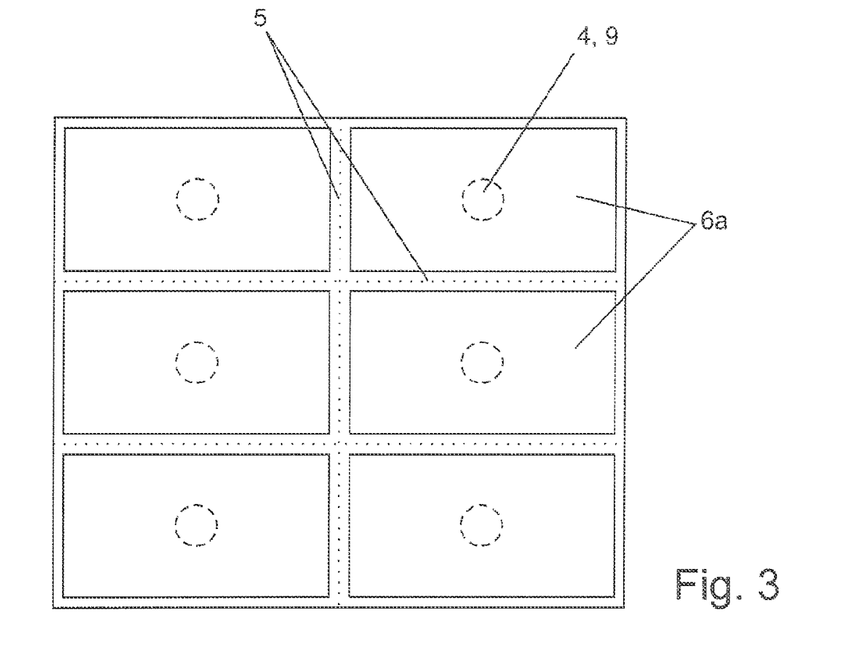
FIG. 3 illustrates a bird's eye view of the insulator layer illustrated in FIG. 2 with the population of a conductor layer as per its first forming.
Figure 4:
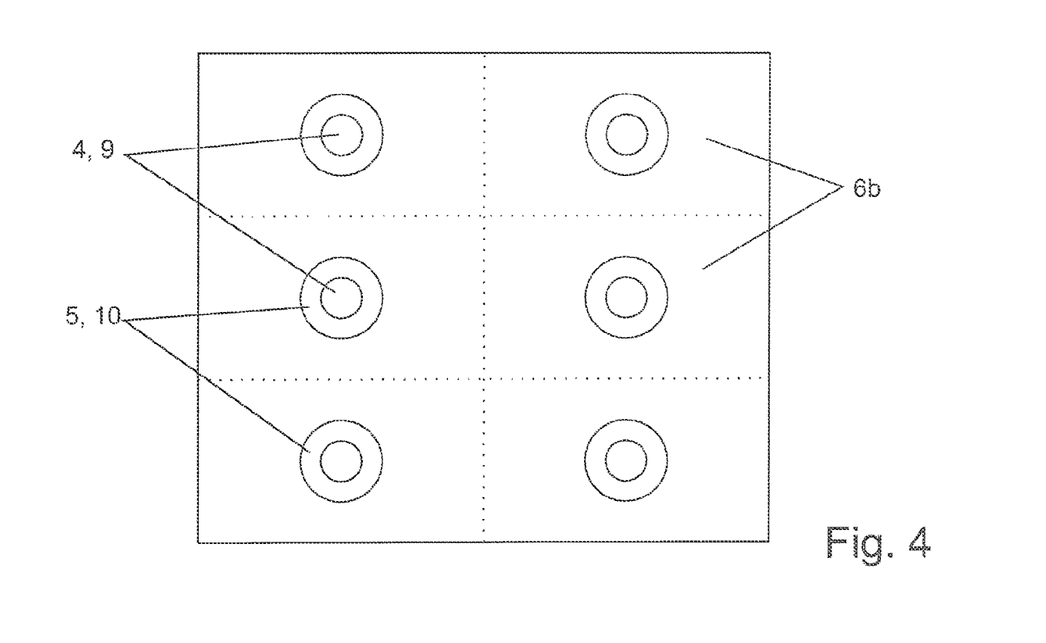
FIG. 4 illustrates a bird's eye view of the insulator layer illustrated in FIG. 2 with the population of a conductor layer as per a second forming.

The following describes a procedure to manufacture a capacitor as illustrated in FIG. 1 and explained in more detail using the drawings in FIG. 2 to FIG. 4.

FIG. 2 illustrates a bird's eye view of an insulator layer, which includes a multitude during the subsequent stacking, in this example a total of 6, of capacitors arranged next to each other in the layer plane. These are separated from each other by means a suitable procedure, like sawing or cutting after stacking the layers and sintering. The separating lines for the subsequent separation are depicted in the drawings FIG. 2 to FIG. 4 by means of dotted lines.

The insulator layer 5 in FIG. 2 is typically provided as a film with a thickness of 100 μm made from a pressed powder as a green body. The preferred range of the thickness of the insulator layer 5 is between 10 μm and 200 μm in one embodiment. As a general embodiment, this insulator layer would include a material with a high dielectricity value, such as barium titanate.

A structure in the shape of breaks 5a permeating the insulator layer 5 is introduced into this insulator layer in the course of a procedural step. In the execution example at hand, which is an especially simple structure of a capacitor, these breaks are shaped like circular holes in the center of the respective insulator layer of the respective capacitor.

The insulator layer structured with breaks is placed on a device for screen printing on top of a vacuum plate (not illustrated). In the following, a template (not illustrated) is placed on top of the insulator layer, which features a hole above the break 5a. After that, a conductive past, such as one based on silver particles, is applied to the template by means of a screen printing procedure and then distributed by means of a squeegee so that the conductive paste is filled into the breaks 5a of the insulator layer 5 through the openings in the template.

In the example at hand, the size of the break 5a is illustrated distorted from its original shape. Especially preferred in one embodiment is for the diameter of the break 5a and the depth of the break 5a (=thickness of the insulator layer 5) to be about the same size. Therefore, a preferred diameter in one embodiment of the break 5a is presented at 0.1 mm.

When applying the conductive paste, the break 5a is filled with the conductive paste and dried afterwards. In this condition (see FIG. 2), the dried filling of the break 5a of the insulator layer 5 forms a segment of the contact body 4 made of conductive material.

In the following, the insulator layer 5 is subjected to another screen print step, where either a conductor layer 6a as per a first formation (see FIG. 3) or a conductor layer 6b as per a second formation (see FIG. 4) is applied.

For the conductor layer 6a, flat capacitor plates are placed, which overlap with the filling of the break 5a or the contact body 4 and which are connected conductively with the contact body 4. In the area of the contact body, a segment 9 of the contact body is also formed by the conductor layers 6a. It is intended for the conductive areas of the conductor layer of the first formation 6a to not reach the separation limits of the different capacitors, but for them to keep an edge distance, which is sufficient to grant insulation.

For the conductor layers as per the second formation 6b, however, it is desired that the conducting layer overlaps the respective separating limits of the capacitors, as these are intended to later reach the sidewall of the later sawed capacitor as ground contacted conductor layers. In order for the conductor layers of the second formation 6b to not get into conductive contact with the contact body 4 and therefore the conductor layers of the first formation 6a, a non-covered area 10 is excluded in their center, which feature a sufficient edge distance to the contact body 4 (see FIG. 4). Also, the conductor layers of the second formation 6b form a segment 9 of contact body 4 in the area of the contact body 4.

After placing the conductor layers 6a, 6b and the respective drying phase, the individual layers can be stacked alternatingly on top of one another. Here, an insulator layer 5 is stacked alternatively on top of a conductor layer of the first formation 6a and an insulator layer 5 is stacked alternatively on a conductor layer of the second formation 6b, until the respective desired number of layers or the construction height of the capacitor 1 is reached. In the course of this stacking process, the contact body 4 is stacked successively with segments of the conductively filled breaks 5a of the insulator layers 5 and the conductor layers 6a, 6b. If applicable, a specially structured upper and/or lower cover layer can be applied to the stack.

This stack consisting of horizontally connected capacitors is then placed into press device, where the individual layers are pressed on top of another in a way that ensures a sufficient contact of the layers for a subsequent sintering procedure.

The thickness of the conductor layers 6a, 6b applied by means of a screen printing process is between 1 μm and 20 μm. The conductor layers 6a, 6b are regularly significantly thinner than the insulator layers 5. It is noted at this point that in connection with the pressing procedure, it is ensured that principally existing hollow spaces that may be caused by not completely flat coverage with conductor layers 6a, 6b between subsequent insulator layers 5 do not pose problems for the stack.

The pressed stack is placed into a sintering oven, where a co-sintering procedure to sinter the conductive pastes and the insulator layers takes place by means of a defined temperature profile.

After leaving the sintering oven and the respective cooling period, the individual capacitors 1 are sawed out of the stack or separated.

Here, the conductor layers of the second formation 6b extend to the side walls of the stack created by the sawing process. In the following, the respective side wall is coated with a conductive layer 7, to connect the conductor layers of the second formation 6b with one another and to allow a connection to a ground line. The ground line can be connected, for example, to another, not illustrated line element of the feedthrough 2 or, depending on the requirements, to a conductive part of the housing (not illustrated).

Per this, each capacitor, whose contact body 4 is plane and flush with its surfaces, is fitted with a contact stud made from a soft soldering material over the ends of the contact body 4. This, for example, can be performed by means of an automatically moved injector.

The capacitor 1 can be fixed and contacted via its contact stud 3, especially by means of a flip chip procedure on a different structure, such as the feedthrough described earlier.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A capacitor, comprising:
    a multitude of insulator layers that are parallel in a stacking direction, consisting of an electrically non-conducting material and that have a thickness in the stacking direction;
    a multitude of conductor layers alternatively layered with the multitude of insulator layers in the stacking direction, the conductor layers made of a conductive material and the conductor layers having a thickness in the stacking direction that is less than the thickness of the multitude of insulator layers;
    at least one conductive contact body comprising a stack of sintered conductive segments, wherein a first formation of conductor layers are connected to each other via the contact body, and wherein conductive segments immediately adjacent the conductor layers have a thickness substantially the same as the thickness of the conductor layers and conductive segments immediately adjacent the multitude of insulator layers have a thickness substantially the same as the thickness of the multitude of insulator layers; and
    at least one side-wall conductive layer attached to the side wall of the capacitor, wherein a second formation of conductor layers are connected to each other via the side-wall conductive layer;
    wherein the contact body extends through breaks of several of the multitude of insulator layers;
    wherein at least the multitude of insulator layers are manufactured from a sintered material; and
    wherein the contact body is manufactured at least partially from a sintered material, which is introduced into the breaks in the multitude of insulator layers in an unsintered, malleable state.

2. The capacitor of claim 1, wherein the entire contact body is positioned perpendicular to the multitude of insulator layers in a long shape.

3. The capacitor of claim 1, wherein at least some of the stack of sintered segments are configured as a filler for one of the break of the multitude of insulator layers.

4. The capacitor of claim 1, wherein the conductor layers consist of a sintered material.

5. The capacitor of claim 4, wherein the multitude of insulator layers, the multitude of conductor layers and the contact body are sintered by means of a co-sintering process.

6. The capacitor of claim 1, wherein a ratio between a thickness between the multitude of insulator layers and a median diameter of the break in the multitude of insulator layers is between 0.1 and 2.

7. The capacitor of claim 1, wherein at least two of the conductive segments comprise different materials.

8. A contact array to be used in the housing of a medically implantable device, comprising:
    an electrical feedthrough with at least on electrically insulating feedthrough base body and at least one electrical conductive line element;
    wherein the line element is configured to create at least one electrically conducting connection between the interior of the housing and an exterior space through the feedthrough base body; and
    an electrical capacitor electrically coupled to the line element of the feedthrough, the electrical capacitor comprising:

a multitude of alternatively layered insulators, of an electrically non-conducting material having a thickness in a stacking direction, and conductor layers, of a conductive material, that are parallel in the stacking direction, the multitude of conductor layers having a thickness in the stacking direction that is less than the thickness of the multitude of insulator layers;

at least one conductive contact body comprising a stack of sintered conductive segments coupled to a first formation of conductor layers of the multitude of conductor layers, and wherein conductive segments immediately adjacent the multitude of conductor layers have a thickness substantially the same as the thickness of the multitude of conductor layers and conductive segments immediately adjacent the multitude of insulator layers have a thickness substantially the same as the thickness of the multitude of insulator layers; and at least one side-wall conductive layer attached to the side wall of the capacitor, wherein a second formation of conductor layers are connected to each other via the side-wall conductive layer;

wherein the contact body extends through breaks of several of the multitude of insulator layers;

wherein at least the multitude of insulator layers are manufactured from a sintered material; and wherein the contact body is manufactured at least partially from a sintered material, which is introduced into the breaks in the multitude of insulator layers in an unsintered, malleable state.

9. The contact array of claim 8, characterized in that the line element of the feedthrough and the contact body of the capacitor are connected to one another conductively via at least one contact stud, where the contact stud consists of a soldered connection.

10. A method of manufacturing a capacitor, comprising:
providing alternating insulator layers and conductive layers on top of one another in a stack, wherein the insulator layers consist of an electrically non-conducting material as a plate- shaped green body and the conductive layer comprise a conductive material, and wherein the insulating layers are thicker than the conductive layers;

wherein providing the insulator layers further comprises forming breaks inside each of the insulator layers and filling in the breaks with a conductive paste;

forming at least one conductive contact body comprising a stack of conductive segments, wherein a first formation of the conductor layers are connected to each other via the contact body, wherein the contact body, in an unsintered, malleable state, extends through the breaks of the insulator layers, and wherein conductive segments immediately adjacent the conductor layers have a thickness substantially the same as the thickness of the conductor layers and conductive segments immediately adjacent the multitude of insulator layers have a thickness substantially the same as the thickness of the multitude of insulator layers;

forming a side-wall conductive layer to a side wall of the stack, wherein a second formation of conductor layers are electrically connected to each other via the side-wall conductive layer; and sintering the stack.

11. The method of claim 10, further comprising separating a multitude of capacitors from the stack.

12. The method of claims 10, further comprising placement a contact stud on one end of the contact body.

13. The method of claim 10, wherein filling in the breaks with conductive paste comprises:
applying a template to the insulator layer, where the template has openings covering the breaks; and
applying conductive paste to the template as is done in screen printing procedures.

14. The method of claim 13, wherein filling in the breaks with conductive paste is supported by a vacuum below the insulator layer.

15. The method of claim 13, characterized in that there is a drying process of the conductive paste after it is applied to the template.

16. The method of claim 13, providing the conductor layer of a conductive material comprises:
applying a template to one of the insulator layers, where the template has openings covering a form of the conductor layer; and
applying conductive paste to the template and creating the conductor layer as is done in screen printing procedures.

17. The method of claim 13, characterized in that the stack is pressed.

* * * * *